United States Patent [19]

Kikuchi et al.

[11] Patent Number: 4,945,051

[45] Date of Patent: Jul. 31, 1990

[54] PRODUCTION OF HUMAN LYSOZYME

[75] Inventors: Masakazu Kikuchi, Toyono; Koji Yoshimura, Osaka; Kazuo Nakahama, Nagaokakyo, all of Japan

[73] Assignee: Takeda Chemical Industries, Ltd., Osaka, Japan

[21] Appl. No.: 65,860

[22] Filed: Jun. 24, 1987

[30] Foreign Application Priority Data

Jun. 30, 1986 [JP] Japan .................. 61-151809
Aug. 20, 1986 [JP] Japan .................. 61-192639
Feb. 23, 1987 [JP] Japan .................. 62-37869

[51] Int. Cl.$^5$ .................. C12N 15/00; C12N 9/36; C12N 1/16; C07H 15/12
[52] U.S. Cl. .................. 435/172.3; 435/206; 435/255; 435/320; 435/942; 536/27; 935/14; 935/28; 935/37; 935/48
[58] Field of Search .................. 435/172.3, 206, 252.3, 435/255; 536/27; 935/14, 48

[56] References Cited

FOREIGN PATENT DOCUMENTS 3163884 2/1985 Australia .
901223 3/1985 Belgium .
0170266 7/1985 European Pat. Off. .
0155189 9/1985 European Pat. Off. .
0181634 5/1986 European Pat. Off. .
0208472 1/1987 European Pat. Off. .
7838386 4/1986 Japan .
7838786 4/1986 Japan .

OTHER PUBLICATIONS

Bennetzen, et al., J. of Biol. Chem. vol. 237, 6, 3/25/82, 3026-3031.
Oberto, J. et al., Gene 40, 57-65 (1985).
Muraki, M., et al., Argric. Biol. Chem. 50(3), 713-723 (1986).
Ikehara et al., Chem. and Pharm. Bull. vol. 34, No. 5, 5/86, pp. 2202-2208.
Jung et al, PNAS (USA), vol. 77, No. 10, 10/80, pp. 5759-5783.
Jigami et al. *GENE* 43: 273-279 (1986).
Kendall et al. *Nature* 321: 706-708 (1986, Jun. 12).
Yoshimura et al. *Biochemical and Biophysical Research Communications* 145: 712-718 (1987, Jun. 15).

*Primary Examiner*—Thomas Mays
*Attorney, Agent, or Firm*—David G. Conlin; Ronald I. Eisenstein

[57] ABSTRACT

A DNA sequence wherein a DNA segment coding for a signal peptide of the formula:

M-R-S-F-L-L-A-L-C-F-L-P-L-A-A-L-G is bound to the 5' end of a DNA segment coding for human lysozyme, a cell transformed with the above DNA sequence and a process for producing human lysozyme, which comprises cultivating the above cell accumulating human lysozyme in the culture and recovering the same are disclosed.

The above techniques make the mass production of human lysozyme useful as pharmaceuticals possible. The present signal peptide is superior to that of hen egg white lysozyme for secretive production of human lysozyme.

8 Claims, 4 Drawing Sheets

```
XhoI         M  R  S  F  L  L  A  L  C  F  L  P  L  A  A  L  G         TaqI
  |    #1    |    #3          |         #5       |       #7       |

TCGAGTATAAAAACAATGAGATCTTTCTTGTTGTTGGCTTTGTGTTTCTTGCCATTGGCTGCTTTGGGTAAGGTTTT

CATATTTTTGTTACTCTAGAAAGAACAACAACCGAAACACAAAGAACGGTAACCGACGAAACCCATTCCAAAAGC
    |   #2    |        #4      |             #6        |       #8       |
```

IMPROVED SIGNAL (pGFL735)

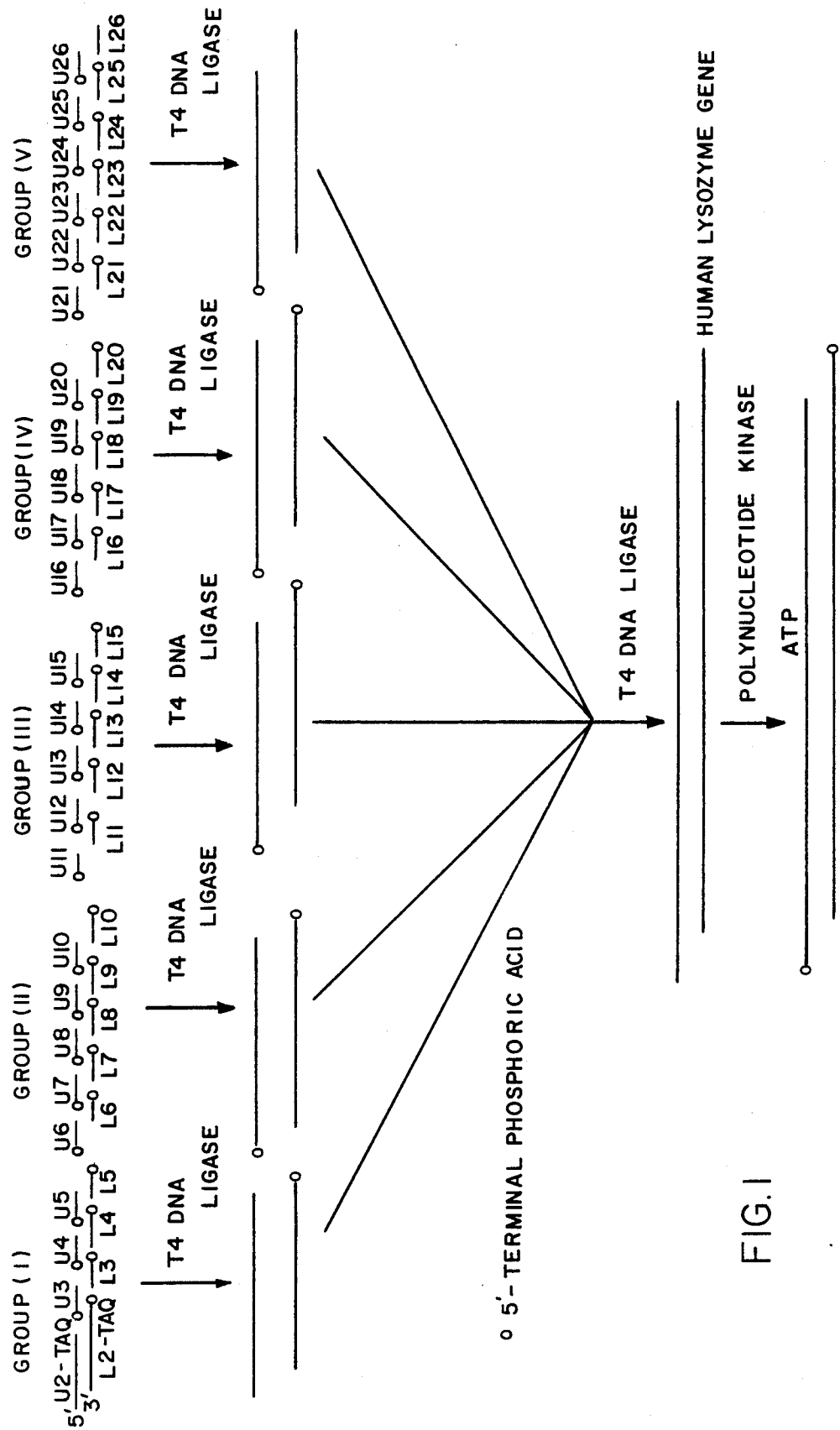
FIG. I

```
TaqI
TCGAGAGATGCGAATTAGCCAGAACTTTGAAGAGATTGGGTATGGACGGCTACCGTGGTATTTC
AGCTCTCTACGCTTAATCGGTCTTGAAACTTCTCTAACCCATACCTGCCGATGGCACCATAAAG

HpaII      MaeIAluI
TTTAGCCAACTGGATGTGTCTTGCTAAGTGGGAATCCGGCTATAACACTAGAGCTACCAATTAC
AAATCGGTTGACCTACACAGAACGATTCACCCCTTAGGCCGATATTGTGATCTCGATGGTTAATG

XbaI
AACGCTGGCGACCGTTCTACAGACTATGGTATTTCCAAATTAACTCTAGATATTGGTGTAACG
TTGCGACCGCTGGCAAGATGTCTGATACCATAAAGGTTTAATTGAGATCTATAACCACATTGC

AluI
ATGGCAAGACTCCAGGTGCCGTCAACGCCTGTCACTTATCTTGCTCAGCTTTGCTTCAGGACAA
TACCGTTCTGAGGTCCACGGCAGTTGCGGACAGTGAATAGAACGAGTCGAAACGAAGTCCTGTT

HhaI
CATTGCTGATGCTGTTGCCTGCGCCTAAGAGAGTTGTCCGTGACCCACAGGGTATTAGAGCCTGG
GTAACGACTACGACAACGGACGCGATTCTCTCAACAGGCACTGGGTGTCCCATAATCTCGGACC

GTCGCTTGGAGAAACAGATGCCAAAATAGAGATGTCAGACAATACGTTCAAGGTTGTGGTGTTT
CAGCGAACCTCTTTGTCTACGGTTTTATCTCTACAGTCTGTTATGCAAGTTCCAACACCACAAA

FIG.2

XhoI
AluI
AATAGCTCGA
TTATCGAGCT
```

Xhol     M R S F L L L A L C F L P L A A L G     TaqI

1    #3    #5    #7

TCGAGTATAAAACAATGAGATCTTTCTTGTTGTTGGCTTTGTTCTTGCCATTGGCTGCTTTGGGTAAGTTTT

CATATTTTGTTACTCTAGAAAGAACAACAACCGAAACACAAGAACGGTAACCGACGAAACCCATTCCAAAAGC

2    #4    #6    #8

IMPROVED SIGNAL (pGFL735)

FIG. 3

CONSTRUCTION OF HUMAN LYSOZYME (h-LZM)-EXPRESSION PLASMID

PRODUCTION OF HUMAN LYSOZYME

BACKGROUND OF THE INVENTION

1. Field of the Invention

This invention relates to recombinant DNA techniques for producing human lysozyme. More particularly, it relates to the expression of the human lysozyme gene, recombinant plasmids, transformed cells, and their products.

2. Description of the Prior Art

Lysozyme is a comparatively small enzyme protein with a molecular weight of approx. 14,000. Lysozyme is distributed in living tissue and is believed to play a role as a defensive substance against bacterial infections by dissolving various bacteria. The method of lysozyme function is thought to involve hydrolysis of polysaccharide of the bacterial cell wall by $\beta$-glucosidase activity. A good deal of lysozyme is contained in hen egg white and lysozyme with high purity can be isolated therefrom comparatively easily. Lysozyme is thus added to cheese, sausage and marine products for their preservation or used for the purpose of converting bovine milk to human maternal milk [Katsuya Hayashi and Taiji Imoto, "Lysozyme", Nankodo, Japan (1974)]. Further, as a medicinal agent, lysozyme is used as a hemostatic, anti-inflammation, tissue regeneration, anti-tumor etc. agent [see for instance "Saikin-no-Shinyaku" (New Drugs in Japan) vol. 34, 107, Yakuji Nippo, Tokyo, Japan, 1983) and it is also on sale as anti-infla-mmatory enzyme agent.

When the lysozyme derived from hen egg white is used for medical purposes, sensitive symptoms such as rash, redness, etc. often result. These are generally regarded as a side effect of the immune response to the presence of a foreign protein. To overcome the above-mentioned disadvantages, the present inventors began studying to establish a means for the mass production of human lysozyme.

Amino acid sequence of human lysozyme is known, and consists of 130 amino acids ["Biochemical Data Book" 1, 189 (1979), editted by Japan Biochemical Association]. On the basis of the amino acid sequence, a DNA fragment coding for the human lysozyme is chemically synthesized [Ikehara, M. et al, Chem. Pharm. Bull. 34, 2202 (1986)].

For the production of human lysozyme using a recombinant DNA technique, Muraki et al tried to express it in *E. coli* but failed to obtain active human lysozyme with such an expression system [Muraki, M. et al, Agric. Biol. Chem. 50, 713 (1986)].

An active human lysozyme has been obtained by secretion using a yeast [Jigami et al, Summary of Japanese Agricultural Chemistry Association 1986, p.343 (1986)]. But the yield is very low, i.e. only 600 μg/liter. According to Jigami et al, a cDNA fragment coding for a signal peptide having information for extracellular secretion of a desired protein is used in combination with a DNA fragment coding for a human lysozyme for the expression of the human lysozyme. Jigami et al uses a cDNA fragment (natural type) coding for a signal peptide of egg white lysozyme [The signal peptide has the same sequence as that disclosed in Pro. Natl. Acad. Sci. U.S.A. 77, 5759–5763 (1980)]. With such a combination, however, the lysozyme is secreted extracellularly from yeast cells in a very small amount as described above.

SUMMARY OF THE INVENTION

The present inventors have made an intensive study to produce active human lysozyme in large amounts by utilizing a recombinant DNA technique and, as a result, have completed the present invention.

Although the human lysozyme gene has not yet been cloned, the amino acid sequence of the human lysozyme has been determined. Thus, Ikehara et al have chemically synthesized a DNA sequence coding for the human lysozyme on the basis of the amino acid sequence [Ikehara, M. et al (supra)].

It is therefore possible to produce the human lysozyme in a large amount by recombinant DNA technique with the use of the chemically synthesized DNA. This amount is greater than about 0.6 mg/l, preferably 0.8 mg/l or greater, more preferably greater than about 3 mg/l, and most preferably greater than about 5 mg/l.

The DNA fragment coding for a signal peptide to be used with the DNA fragment coding for the human lysozyme, includes a DNA fragment coding for a signal peptide containing a sufficient number of amino acids of the formula:

M-R-S-F-L-L-A-L-C-F-L-P-L-A-A-L-G to exhibit signal peptide properties. Preferably the DNA segment codes for the amino acids of the above formula.

In expression in a yeast, a DNA fragment coding for signal peptide prepared by preferentially using codons which are used very frequently in yeast. With such a DNA fragment, the desired object, namely obtaining human lysozyme in a large amount, has been found to be accomplished. Codon usage is reported in The Journal of Biological Chemistry 257, 3026–3031 (1982). Examples of preferable codons for yeast are given below in terms of codons for RNA.

| Amino acid | Codon | Amino acid | Codon | Amino acid | Codon |
|---|---|---|---|---|---|
| Ala | GCU, GCC | His | CAC | Tyr | UAC |
| Ser | UCU, UCC | Glu | GAA | Cys | UGU |
| Thr | ACU, ACC | Gly | GGU | Asn | AAC |
| Val | GUU, GUC | Gln | CAA | Pro | CCA |
| Ile | AUU, AUC | Lys | AAG | Met | AUG |
| Asp | GAC | Leu | UUG | Trp | UGG |
| Phe | UUC | Arg | AGA | | |

BRIEF DESCRIPTION OF THE DRAWINGS

FIG. 1 is a diagram showing a method for the synthesis of the human lysozyme gene by collecting and ligating oligonucleotides;

FIG. 2 shows a DNA sequence of the TaqI-XhoI fragment of the human lysozyme gene;

FIG. 3 shows a DNA sequence of the signal peptide;

DESCRIPTION OF THE PREFERRED EMBODIMENTS

Figure 4:
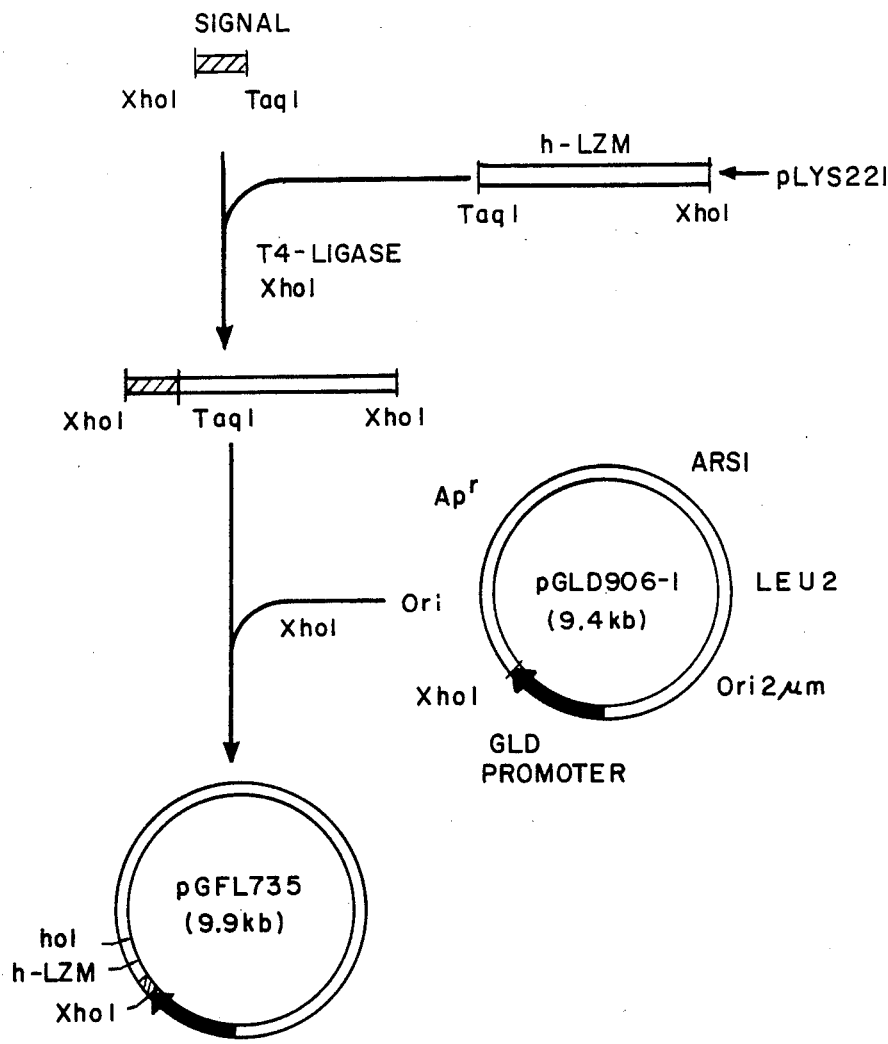
FIG. 4 shows a scheme for the construction of a human lysozyme secretion plasmid.

In preparing the synthetic gene according to Ikehara et al, a DNA sequence is selected with the consideration of the following points:

(i) The most preferable codons in yeast which is considered suitable for expression of synthetic gene are used. (ii) A specific recognition site of restriction enzyme (Xba I for example) is made to serve as a marker for cloning or to fascilitate reconstruction of the gene after constructing an expression vector, (iii) Sequences which are self-complementary, or complementary with an undesired sequence in either strand or both strands are avoided.

The human lysozyme gene can be chemically synthesized as described above.

It is necessary to insert the synthetic gene in a proper vector for sub-cloning to enrich it. Though any kind of vector may be used wherein this gene can be inserted, *Escherichia coli* vector pACYC177, *Escherichia coli*-yeast shuttle vector pPHO17, pGLD906 and pGLD906-1 (Japanese Patent Unexamined Publication No. 61-43991) and *Bacillus subtilis* vector pTEX201 [Yoshimura, K. et al, Appl. Microbiol. Biotechnol. 23, 250 (1986)] are cited as specific examples.

Various host organisms are transformed by using vectors containing synthetic genes thus obtained. The method of transformation itself is well known, but when *Escherichia coli* is used as a host organism, transformation can be performed by the method of Cohen et al., [Cohen, S. N. et al., Proc. Natl. Acad. Sci. U.S.A., 69, 2110 (1972)], when yeast is used as a host organism, transformation can be performed by the method of Hinnen et al., Hinnen A et al., Proc. Natl. Acad. Sci. U.S.A., 75, 1927 (1978)] and when *Bacillus subtilis* is used as a host organism, transformation can be performed by protoplast method [Chang, S. & Cohen S. N. Gen. Genet., 168, 111 (1979)] or competent method [Dubnau, D. & Abelson, R. D., J. Mol. Biol. 56, 209 (1971)], respectively. As host organisms, for instance, *E. coli* 294, *E. coli* W3110, *E. coli* C600, *Saccharomyces cerevisiae* AH22R⁻, *B. subtilis* 1A1, *B. subtilis* 1A339, *B. subtilis* 1A340 may be used.

Then, in order to express the gene, the plasmid DNA in which the gene is inserted is first isolated from the transformants by for example, an alkaline extraction method [Birnboim, H. C. & Doly, J.: Nucleic Acids Res., 7, 1513 (1979)]. By treating plasmid DNA thus obtained with proper restriction enzyme the inserted gene can be cut out and can be isolated by agarose gel electrophoresis or poly-acrylamide gel electrophoresis. All of these processes are well known and they are mentioned in literature in detail [see for example Molecular Cloning (1982), Cold Spring Harbor Laboratory]. The isolated gene is linked downstream from a promoter and signal peptide-coding region in an appropriate expression vector in the correct direction to construct an expression plasmid.

As a preferred DNA sequence coding for the signal peptide, there may be mentioned a DNA segment chemically synthesized on the basis of codon usage for yeast. Although preferable codons of the chemically synthesized DNA are those which are most frequently used in yeast, codons in lower frequency may be used for the preparation of restriction enzyme recognition site(s). The DNA may be chemically synthesized, for example, by the method of Crea et al [Crea, R. et al, Proc. Natl. Acad. Sci. U.S.A. 75, 5765 (1978).

A DNA fragment wherein a DNA segment which codes for signal peptide is bound to the 5'-end of a DNA segment coding for human lysozyme may be prepared by linking a DNA fragment coding for the signal peptide to 5'-end of the DNA segment coding for human lysozyme, as mentioned previously.

The DNA fragment can also be prepared (a) by linking a DNA segment coding for signal peptide and a portion of N-terminus of human lysozyme with a DNA segment coding for human lysozyme lacking the portion of N-terminus thereof, (b) by linking a DNA segment coding for signal peptide lacking a portion of C-terminus thereof with a DNA segment coding for the portion of C-terminus of signal peptide and for human lysozyme, or (c) by linking a DNA segment coding for signal peptide lacking a portion of C-terminus thereof, a DNA segment coding for the portion of C-terminus of signal peptide and for a portion of N-terminus of human lysozyme and a DNA segment coding for human lysozyme lacking the portion of N-terminus thereof.

A number of expression vectors are known in the art. Any of them can be used as long as they are suitable for the expression of the gene. Illustrative of suitable expression vectors are pPHO17, pGLD906, pGLD906-1 (supra), pcDX [Okayama, H. & Berg, P., Mol. Cell. Biol. 3, 280 (1983) and pKSV-10 (manufactured by Pharmacia Inc.).

As the promoter, PHO5 promoter, GLD promoter, PGK promoter, ADH promoter, PHO81 promoter, for example, may be used when a yeast is used as host. When an animal cell is used as a host cell, SV40 early gene promoter, metallothionein promoter and heat shock promoter, for example, may be used as the promoter.

The utilization of an enhancer is also effective for expression.

The host cell to be used for expression, includes yeasts such as *Saccharomyces cerevisiae*, mouse L cells and Chinese hamster oocyte cells. Other eukaryotic cells may be used, however.

A method of transforming a yeast has been previously described. A method of transforming eukaryotic cells such as animal cells is described in, for example, "Proteins, Nucleic Acids and Enzymes 28, (1983), Introduction of Recombinant DNA Into Cells and Expression Thereof" (Kyoritsu Shuppan).

Using the thus obtained secreting plasmid, host cells are transformed, thereby to obtain a desired transformant. The transformant is then cultivated in any known manner.

A culture medium to be used for yeasts may be, for example, Burkholder minimum medium [Bostian, K. L. et al, Proc. Natl. Acad. Sci. U.S.A. 77, 4505 (1980), Amer, J. Bot. 30, 206 (1943)] or its modified media. The cultivation may be generally conducted at a temperature of 15°–40° C., preferably 24°–37° C. for a period of time of 10–96 hours, desirably 24–72 hours, more preferably about 50–72 hours, with aeration and/or agitation if necessary.

When a transformant for which an eukaryotic cell such as an animal cell is used as host is cultured, Eagle's MEM [H. Eagle, Science 130, 432 (1959)], modified Eagle's medium of Dulbecoo [Orgad Larb & William J. Ritter, J. Biol. Chem. 258, 6043 (1983)], or the like may be used as a culture medium. The cultivation may be generally conducted at a temperature of 30°–42° C., preferably 35°–37° C. for about 1–10 days.

After the completion of the cultivation, cells and the supernatant are separated by well known methods. To collect human lysozyme remaining within the cells, the cells are disrupted by any conventional method, such as disruption with ultrasonication or a French press, a mechanical disruption such as crushing and a disruption with lytic enzyme. Further if necessary, human lysozyme thus prepared may be extracted by surface active agents such as Triton-X100 and deoxycholate. The human lysozyme in supernatant or extract thus prepared is purified by conventional protein purification methods such as salting out, isoelectric point precipitation, gel filtration, ion-exchange chromatography and high performance liquid chromatography (HPLC, FPLC, etc.) to obtain the desired human lysozyme.

A human lysozyme has medicinal activities such as anti-inflammation, hemostasis, tissue regeneration and anti-tumor and is used as an antiphlogistic enzyme agent for eye lotion or as an anticeptic agent for foods. When used for pharmaceutical purposes, the human lysozyme does not exhibit such side effects that are caused in the case of hen egg white lysozyme due to immune response. Hitherto, however, the human lysozyme has been only obtained in a small amount. This method makes it possible to produce recombinant human lysozyme in amounts greater than 0.6 mg/l. Preferably, it can be produced in amounts of 0.8 mg/l or greater, more preferably greater than about 3 mg/l, and most preferably greater than about 5 mg/l.

The present invention makes it possible to provide a large amount of human lysozyme useful as pharmaceuticals as described above. The signal peptide of the present invention is superior to the signal peptide of egg white lysozyme for secretion production of human lysozyme.

Reference Example 1

Construction of Cloning Vector pBR322X

After 5 μg of *Escherichia coli* vector pBR322 was reacted with 1.5 units of restriction enzyme BalI in 40 μl of reaction buffer [10 mM Tris-HCl (pH7.5), 10 mM MgCl$_2$, 1 mM dithiothreitol] at 37° C. for 5 hours, the reaction mixture was extracted with phenol and DNA was precipitated with ethanol in accordance with conventional methods. 50 ng of phosphorylated Xho I linker d[pCCTCGAGG] (New England Biolabs) was added to this DNA and they were ligated with each other by T4 DNA ligase according to conventional methods. With this reaction solution *Escherichia coli* DH1 was transformed and plasmids were extracted from thus obtained ampicillin-resistant and tetracycline-resistant colonies according to the alkaline extraction method (previously mentioned) to obtain plasmid pBR322X with Xho I site in place of Bal I site.

Reference Example 2

Preparation of Human Lysozyme Gene Fragment Bearing TaqI site around N-terminus

In the report of Ikehara et al (supra) the human lysozyme gene is prepared from the 52 oligonucleotide blocks shown in Table 1.

TABLE 1

| Upper Strand No. | | Lower Strand No. | |
|---|---|---|---|
| U1 | TCGAGATGAAGGTTT | L26 | TCGAGCTATTAAAC |
| U2 | TTGAGAGATGCGAAT | L25 | ACCACAACCTTGAAC |
| U3 | TAGCCAGAACTTTGAAG | L24 | GTATTGTCTGACATC |
| U4 | AGATTGGGTATGGAC | L23 | TCTATTTTGGCATCT |
| U5 | GGCTACCGTGGTATT | L22 | GTTTCTCCAAGCGAC |
| U6 | TCTTTAGCCAACTGG | L21 | CCAGGCTCTAATACCCTG |
| U7 | ATGTGTCTTGCTAAG | L20 | TGGGTCACGGACAAC |
| U8 | TGGGAATCCGGCTATAAC | L19 | TCTCTTAGCGCAGGC |
| U9 | ACTAGAGCTACCAAT | L18 | AACAGCATCAGCAAT |
| U10 | TACAACGCTGGCGAC | L17 | GTTGTCCTGAAGC |
| U11 | CGTTCTACAGACTATGG | L16 | AAAGCTGAGCAAGAT |
| U12 | TATTTTCCAAATTAACT | L15 | AAGTGACAGGCGTTGAC |
| U13 | CTAGATATTGGTG | L14 | GGCACCTGGAGTCTTGC |
| U14 | TAACGATGGCAAGACTC | L13 | CATCGTTACACCAATAT |
| U15 | GAGGTGCCGTCAACGCC | L12 | CTAGAGTTAATTTGG |
| U16 | TGTCACTTATCTTGC | L11 | AAAATACCATAGTCTGT |
| U17 | TCAGCTTTGCTTCAG | L10 | AGAACGGTCGCCAGC |
| U18 | GACAACATTGCTGAT | L9 | GTTGTAATTGGTAGC |
| U19 | GCTGTTGCCTGCGCT | L8 | TCTAGTGTTATAGCCG |
| U20 | AAGAGAGTTGTCCGT | L7 | GATTCCCACTTAGCAAG |
| U21 | GACCCACAGGGTATT | L6 | ACACATCCAGTTGGC |
| U22 | AGAGCCTGGGTCGCT | L5 | TAAAGAAATACCACG |
| U23 | TGGAGAAACAGATGC | L4 | GTAGCCGTCCATACC |
| U24 | CAAAATAGAGATGTC | L3 | CAATCTCTTCAAAGT |
| U25 | AGACAATACGTTCAAGG | L2 | TCTGGCTAATTCGCATC |
| U26 | TTGTGGTGTTTAATAGC | L1 | TCTCAAAAACCTTCATC |

EXAMPLE

The present invention will be illustrated in more detail hereinbelow by way of Reference Examples and Examples. These examples are, however, not to be considered as limiting the scope of the invention.

*Sacchromyces cerevisiae* AH22R$^-$/pGLF735 disclosed in Example 3 has been deposited at IFO (Institution for Fermentation, Osaka, Japan) under the designation of IFO-10227 and since Feb. 5, 1987 with FRI (Fermentation Research Institute, Agency of Industrial Science and Technology, Ministry of International Trade and Industry, Japan) under the designation of FERM P-9173, and the deposit has been changed to the deposit according to Budapest Treaty and stored at FRI under the accession number of FERM BP-1346.

In Table 1, CGAGAGATGCGAAT in place of U2 and TCTGGCTAATTCGCATCTCT in place of L2 were synthesized as U2-taq and L2-taq respectively according to the report of Ikehara et al. Then using each fragment U2-taq, U3 to U26, L2-taq, L3 to L26, hybrid of oligonucleotide blocks was formed according to the report of Ikehara et al (FIG. 1). After each of these groups were linked according to the method stated in Example 1, both 5'-ends were enzymatically phosphorylated.

Reference Example 3

Sub-cloning of Fragment of Human Lysozyme Gene containing Taq I Site 2.6 μg of plasmid pBR322X constructed at Reference Example 1 was reacted with 6 units of restriction enzyme XhoI and 6 units of restriction enzyme ClaI in 35 μl of a reaction solution [33 mM acetate buffer, pH 7.9, 66 mM potassium acetate, 10 mM magnesium acetate, 0.5 mM dithiothreitol, 0.01% BSA (bovine serum albumin)] at 37° C. for 1 hour and the solution was deproteinized with phenol and precipitated with cold ethanol. This DNA (200 ng) was mixed with 100 ng of human lysozyme gene fragment prepared in Reference Example 2 and allowed to react in 10 μl of reaction solution [66 mM Tris-HCl (pH 7.6), 10 mM ATP, 10 mM spermidine, 100 mM MgCl$_2$, 150mM DTT, 2 mg/ml BSA, 5 units of T4 DNA ligase] at 14° C. overnight to be ligated with each other. Using this reaction solution *Escherichia coli* DH1 was transformed according to the method by Cohen et al. Plasmids were isolated from transformants thus obtained according to the alkaline extraction method (previously mentioned). Their molecular weight and cleavage pattern with restriction enzymes were examined and pLYS 221 in which the human lysozyme gene fragment was inserted was obtained. As the result of isolating EcoRI-XhoI fragment of pLYS221 and determining its base sequence in accordance with dideoxynucleotide chain termination method, TaqI-XhoI fragment of human lysozyme gene was obtained as shown in FIG. 2 exactly as assumed.

This sequence codes for the fourth Glu to the 130th Val of amino acid sequence of human lysozyme.

Example 1

Preparation of DNA fragment Coding for Signal Sequence

The fourth leucine, the sixth isoleucine and the eighth valine of the known amino acid sequence of signal peptide of egg white lysozyme [Jung, A. et al, Proc. Natl. Acad. Sci. 77, 5759 (1980)], were replaced by phenylalanine, lencine and alanine respectively. Further to obtain high expression, the nucleotide sequence was prepared based upon the following:

(1) Codons which are used very frequently in yeast are preferentially selected;

(2) To enhance the expression, a sequence of the yeast PGK gene is used upstream of ATG; and (3) Construction of a hybrid signal is possible.

The nucleotide sequence thus synthesized is shown in FIG. 3. As shown, there are provided an XhoI site at the 5'-end a TaqI site at the 3'-end containing the lysozyme encoding region. The entire sequence consists of eight oligonucleotide blocks (#1–#8) which were prepared by the phosphamide method [Caruthers, M. H. et al; Tetrahedron Letters 22, 1859 (1981)].

The nucleotide blocks #2 to #7 [each 10 μl (5 μg)] were mixed with each other, to which were further added 20 μl of a kinase buffer of a 10-fold concentration (0.5M Tris-HCl, 0.1M MgCl$_2$, 0.1M mercaptoethanol, pH 7.6), 20 μl of 10 mM ATP, 20 μl (50 u) of T4 polynucleotide kinase (manufactured by Takara Shuzo Inc.) and 80 μl of distilled water. The mixture was then reacted at 37° C. for 2 hours and thereafter treated at 65° C. for 20 minutes to stop the reaction. To the reaction mixture were added 10 μl (5 μg) of each of the nucleotide blocks #1 and #8 and 10 μl of T4 ligase (manufactured by NEB Inc.) and the mixture was reacted at 14° C. overnight. The resulting reaction mixture was electrophoresed on 10% polyacrylamide gel. A fragment of 76 bp was cut out of the gel and extracted from the gel by electroelution. This was dissolved in 45 μl of distilled water, to which 6 μl of a kinase buffer of a 10-fold concentration (supra), 6 μl of 10 mM ATP and 2 μl (5 u) of T4 polynucleotide kinase (supra) were added. The mixture was reacted at 37° C. for 1 hour and then stored at −20° C.

In FIG. 3, there is adopted a single letter expression for amino acids (Rule Confirmed by IUPAC-IUB Biochemistry Nomenclature).

| Example: | |
|---|---|
| A: | Alanine |
| B: | Aspartic acid or Asparagine |
| C: | Cysteine |
| D: | Aspartic acid |
| E: | Glutamic acid |
| F: | Phenylalanine |
| G: | Glycine |
| H: | Histidine |
| I: | Isoleucine |
| K: | Lysine |
| L: | Leucine |
| M: | Methionine |
| N: | Asparagine |
| P: | Proline |
| O: | Glutamine |
| R: | Arginine |
| S: | Serine |
| T: | Threonine |
| V: | Valine |
| W: | Tryptophan |
| Y: | Tyrosine |
| Z: | Glutamic acid or Glutamine |
| X: | Unknown or other amino acids |

Example 2

Construction of Secretion Expression Plasmid

The plasmid pLYS221 (236 μg) obtained in Reference Example 3 was treated with 120 u of EcoRI (manufactured by Nippon Gene Inc.) and 120 u of XhoI (manufactured by Nippon Gene Inc.) at 37° C. for 2 hours to cut out a fragment of the human lysozyme-encoding region. The fragment was further treated with 26 u of TaqI (manufactured by Nippon Gene Inc.) at 65° C. for 1 hour to obtain a fragment of the human lysozyme-encoding region which lacked a portion of the N-terminal portion.

About 1 μg of the resulting fragment was mixed with 0.5 μg of the signal sequence-encoding DNA obtained in Example 1 and the mixture was reacted in the presence of 800 u of T4 ligase (supra) at 16° C. for 16 hours, followed by a treatment with XhoI (42 u).

The thus obtained XhoI fragment (10 ng) was mixed with 1 ng of a DNA sequence obtained by treating yeast expression vector pGLD906-1 (Japanese Patent Unexamined Publication No. 61-43991) with XhoI, and both were ligated in the presence of T4 ligase.

*E. coli* DH1 was transformed with the reaction mixture in the same manner as above to obtain a number of plasmids containing a GLD promoter, downstream of which the signal sequence-encoding region and the human lysozyme gene were inserted in the same direction as that of the promoter. One of such plasmids was named pGFL735 and used in the following tests (see FIG. 4).

Example 3

Preparation of Yeast Transformant

With the plasmid pGFL735 obtained in Example 2 *Saccharomyces cerevisiae* AH22R⁻ was transformed in accordance with the method of Hinnen et al (supra) to obtain a transformant *Saccharomyces cerevisiae* AH22R⁻/pGFL735.

Example 4

Cultivation of the Transformant

Into a test tube was poured 5 ml of Barkholder modified medium III [Amer. J. Bot. 30, 206 (1943); $KH_2PO_4$ 0.44 g/l, glucose 11 g/l, asparagine 5.6 g/l, sucrose 89 g/l], to which the transformant *S. cerevisiae* AH22R⁻/pGFL735 was innoculated, and cultivation was carried out at 30° C. for 3 days with shaking. One (1) ml of the culture was transferred to another test tube containing 4 ml of the same culture medium and cultivation was performed at 30° C. for one day with shaking. Two (2) ml of the culture was further transferred to a 200 ml flask containing 18 ml of the same Burkholder modified medium III and the mixture was cultivated at 30° C. for 4 days with shaking. During the cultivation, sampling was made at times of 24, 50 and 72 hours.

Example 5

Measurement of Amount of Human Lysozyme Produced

The culture obtained in Example 4 was centrifuged, and the obtained supernatant was assayed for the human lysozyme.

The measurement of the human lysozyme activity was carried out according to Worthigton Enzyme Manual, p. 100, Worthington Biochemical Corporation, USA, 1972. As a standard, human lysozyme manufactured by Sigma Inc. was used "One unit" is defined as the amount of the enzyme required to reduce the absorbance at 450 mμ by 0.001 by reaction at 25° C. for 1 minute in 0.1M phosphate buffer (pH 6.2) using *Micrococcus lysodeikticus* (Sigma) as a substrate. The amount of the human lysozyme produced was as follows:

| Cultivation time | Human Lysozyme (mg/l) Supernatant |
|---|---|
| 24 | 0.8 |
| 50 | 3.2 |
| 72 | 5.2 |

Example 6

Purification and Isolation of Expressed Human Lysozyme

The transformant *S. cerevisiae* AH22R⁻/pGFL735 was first cultivated in a similar method to that described in Example 4.

The obtained culture (1.9 l) was centrifuged, and the supernatant thus obtained was adsorbed to CM-Cellulose column (φ 1.6 cm × 12.5 cm) equilibrated with 50 mM Na-phosphate buffer (pH 6.5). After rinsing the column with 150 ml of the above buffer, the human lysozyme was obtained as an almost single peak by elution with the above buffer containing 0.5M NaCl. The recovery rate was found to be about 70%.

The human lysozyme obtained above was applied to HPLC for further purification. Thus, 0.25 ml of the eluate containing 0.2 mg of the human lysozyme was applied on TSK gel ODS 120T. After rinsing with water +0.1% trifluoroacetic acid (TFA), elution was carried out by a 0–100% gradient method containing $CH_3CN$ in 0.1% TFA to obtain homogeneous human lysozyme.

Example 7

Properties of Human Lysozyme (i) Molecular weight:

The protein obtained in Example 6 was treated with 2-mercaptoethanol and applied to SDS-polyacrylamide gel (15%) electrophoresis (180 V, 2 hours). A Coomassie Brilliant Blue staining revealed a single band of the protein. This band showed the same phoresed distance as that of the human lysozyme specimen electrophoresed simultaneously therewith. Therefore, the protein was expected to have a molecular weight of 14.7 kd which was identical with the human lysozyme.

(ii) Amino Terminal Amino Acid Sequence:

The protein obtained in Example 6 was subjected to an automated Edman degradation [J. Biol. Chem. 256, 7990 (1981)] using a vapor phase protein sequencer (model 470A manufactured by Applied Biosystem Inc.) to analyze the amino terminal amino acid sequence. The yielded phenylthiohydantoin-amino acids (PTH-amino acids) were identified and quantitatively analyzed by means of high performance liquid chromatography (manufactured by Varian Inc.) using a Micropack SPC 18-3 column to give the results shown in Table below. Thus, it was revealed that the amino acid sequence was H-Lys-Val-Phe-Glu-Arg-X-Glu-Leu-Ala-Arg-(X: UNIDENTIFIED).

| Cycle | PTH-Amino Acid (pmole) | (%) |
|---|---|---|
| 1 Lys | 1071 | 57.4 |
| 2 Val | 1176 | 63.0 |
| 3 Phe | 1013 | 54.3 |
| 4 Glu | 1043 | 55.9 |
| 5 Arg | —* | — |
| 6 X** | — | —. |
| 7 Glu | 1046 | 56.0 |
| 8 Leu | 1106 | 59.2 |
| 9 Ala | 1246 | 66.7 |
| 10 Arg | —* | — |

*Uncalculated
**Unidentified (iii) Amino Acid Composition:

The protein obtained in Example 6 was placed in a glass tube for hydrolysis and dried in vacuo. Then, 6N HCl or 4% thioglycolic acid-containing 6N HCl was added into the test tube and sealed in vacuo. Hydorlysis was carried out at 110° C. for 24 hours. After hydrolysis, the hydrochloric acid was removed in vacuo and the residue was dissolved in 0.02N HCl to conduct amino acid analysis. The amino acid analytical values were obtained by taking an average of the values obtained for the two kinds of the hydrolyses. However, for tryptophan, the value obtained in the hydrolysis with 4% thioglycolic acid-containing hydrochloric acid was adopted. The results are shown in the Table below.

| Amino Acid | Amino Acid Composition | | |
|---|---|---|---|
| | Analysis Value | Found* | Theoretical |
| Asp | 0.7475(μmol) | 18 | 18 |
| Thr | 0.2153 | 5.2 | 5 |
| Ser | 0.2324 | 5.6 | 6 |
| Glu | 0.3972 | 9.6 | 9 |
| Pro | 0.0561 | 1.4 | 2 |
| Gly | 0.4652 | 11.2 | 11 |
| Ala | 0.5925 | 14.3 | 14 |
| Half Cys | —** | — | 8 |
| Val | 0.3550 | 8.5 | 9 |
| Met | 0.0823 | 2.0 | 2 |
| Ile | 0.2025 | 4.9 | 5 |
| Leu | 0.3415 | 8.2 | 8 |
| Tyr | 0.2550 | 6.1 | 6 |
| Phe | 0.0839 | 2.0 | 2 |
| Lys | 0.2168 | 5.2 | 5 |
| His | 0 0412 | 1.0 | 1 |
| Arg | 0.5723 | 13.8 | 14 |
| Trp | 0.2032 | 4.9 | 5 |

*Calculated with the value for Asp as 18
**Unmeasured

As described above, the amino acid composition of human lysozyme obtained in the Example is in good conformity with the theoretical values of the amino acid composition of human lysozyme. Accordingly, the human lysozyme obtained in the example is considered to be a natural type human lysozyme.

The following references, which are referred to for their disclosures at various points in this application, are incorporated herein by reference.

Hayashi et al., "Lysozyme", Nankodo, Japan (1974)
Saikin-no-Shinyaku vol. 34 107 Yakuji Nippo, Tokyo Japan (1983)
Biochemical Data Book 1, 189 (1979)
Chem. Pharm. Bull, 34, 2202 (1986)
Agric. Biol. Chem. 50, 713 (1986)
Summary of Japanese Agricultural Chemistry Association 1986, P. 343 (1986)
Pro. Natl. Acad. Sci. USA 77, 5759-5763 (1980)
The Journal of Biological Chemistry 257, 3026-3031 (1982)
Japanese Patent Unexamined Publication No. 61-43991
Appl. Microbiol, Biotechnol, 23, 250 (1986)
Pro. Natl. Acad. Sci. USA, 69, 2110 (1972)
Pro. Natl. Acad. Sci. USA, 75, 1927 (1978)
Gen. Genet., 168, 111 (1979)
J. Mol. Biol. 56, 209 (1971)
Nucleic Acids Res., 7, 1513 (1979)
Molecular Cloning (1982)
Proc. Natl. Acad. Sci. USA 75, 5765 (1978)
Mol. Cell. Biol. 3, 280 (1983)
Proteins, Nucleic Acids and Enzyme 28, (1983)
Proc. Natl. Acad. Sci. USA 77, 4505 (1980)
Amer. J. Bot. 30, 206 (1943)
Science 130, 432 (1959)
J. Biol. Chem. 258, 6043 (1983)
Tetrahedron Letters 22, 1859 (1981)
J. Biol. Chem. 256, 7990 (1981)

We claim:

1. A purified and isolated DNA sequence for use in a yeast cell comprising a DNA segment coding for a signal peptide of the formula:

M-R-S-F-L-L-L-A-L-C-F-L-P-L-A-A-L-G functionally linked to the 5' end of a DNA segment coding for human lysozyme.

2. The DNA sequence according to claim 1, wherein the DNA segment coding for the signal peptide has the sequence:

AT-
GA-
GATCTTTCTTGTTGTTGGCTTTTGGTTT-
CTTGCCATTGGCTGCTTTGGGT

TACTCTAGAAAGAACAACAACC-
GAAACACAAAGAACGGTAACCGAC-
GAAACCA.

3. A DNA sequence according to claim 1, which is pGFL 735.

4. A yeast cell transformed with a DNA sequence which comprises a DNA segment coding for a signal peptide of the formula:

M-R-S-F-L-L-L-A-L-C-F-L-P-L-A-A-L-G functionally linked to the 5' end of a DNA segment coding for human lysozyme.

5. A transformed yeast cell according to claim 4, which is Saccharomyces cerevisiae AH22R−/pGFL735 (FERM BP-1346).

6. A process for producing human lysozyme, which comprises cultivating a yeast cell transformed with a DNA sequence which comprises a DNA segment coding for a signal peptide of the formula:

M-R-S-F-L-L-L-A-L-C-F-L-P-L-A-A-L-G functionally linked to the 5' end of a DNA segment coding for human lysozyme in a culture medium, accumulating human lysozyme in the culture medium and recovering human lysozyme.

7. A process according to claim 6, wherein the transformed yeast cell is Saccharomyces cerevisiae AH22R−/pGFL735 (FERM BP-1346).

8. A purified and isolated DNA sequence for use in a yeast cell which comprises a DNA segment coding for a signal peptide of the formula:

M-R-S-F-L-L-L-A-L-C-F-L-P-L-A-A-L-G.

* * * * *